(12) United States Patent  
Nguyen

(10) Patent No.: US 10,531,791 B2  
(45) Date of Patent: Jan. 14, 2020

(54) SELF-CLEANING DENTAL MIRRORS

(71) Applicant: Utralight Optics, Inc., Costa Mesa, CA (US)

(72) Inventor: Ronald C. Nguyen, Fountain Valley, CA (US)

( * ) Notice: Subject to any disclaimer, the term of this patent is extended or adjusted under 35 U.S.C. 154(b) by 0 days.

(21) Appl. No.: 14/210,425

(22) Filed: Mar. 13, 2014

(65) Prior Publication Data
US 2014/0315143 A1 Oct. 23, 2014

Related U.S. Application Data

(60) Provisional application No. 61/780,808, filed on Mar. 13, 2013.

(51) Int. Cl.
*A61B 1/247* (2006.01)

(52) U.S. Cl.
CPC .................... *A61B 1/247* (2013.01)

(58) Field of Classification Search
CPC ..... A61C 1/052; A61C 1/0061; A61C 1/0084; A61C 17/0217; A61C 17/043
USPC .......................................................... 433/31
See application file for complete search history.

(56) References Cited

U.S. PATENT DOCUMENTS

| | | | | |
|---|---|---|---|---|
| 2,984,009 A | * | 5/1961 | Codoni | A61B 1/253 359/509 |
| 2,984,909 A | | 5/1961 | Johnston | |
| 3,006,073 A | * | 10/1961 | McCarter | A61B 1/253 359/509 |
| 3,027,644 A | * | 4/1962 | Piscitelli | A61B 1/253 359/509 |
| 3,048,924 A | | 8/1962 | Whitman et al. | |
| 3,052,031 A | | 9/1962 | Piscitelli | |
| 3,091,034 A | * | 5/1963 | Piscitelli | A61B 1/253 359/509 |
| 3,118,231 A | | 1/1964 | Rathsmill | |
| 3,137,071 A | | 6/1964 | Armstrong | |
| 3,164,904 A | | 1/1965 | Barnes | |
| 3,349,490 A | * | 10/1967 | Lieb | A61C 1/05 433/105 |
| 3,352,305 A | * | 11/1967 | Freedman | A61B 1/247 128/200.19 |
| 3,849,889 A | * | 11/1974 | Rosander | A61B 1/247 433/30 |
| 3,969,824 A | | 7/1976 | Widen et al. | |
| 3,986,266 A | * | 10/1976 | Vellender | A61B 1/253 433/30 |
| 4,279,594 A | * | 7/1981 | Rigutto | A61B 1/253 433/31 |
| 4,400,157 A | * | 8/1983 | Moore | A61B 1/253 433/31 |
| 4,629,425 A | * | 12/1986 | Detsch | A61B 1/253 433/29 |
| 5,139,420 A | * | 8/1992 | Walker | A61B 1/253 433/31 |
| 5,449,290 A | * | 9/1995 | Reitz | A61B 1/253 433/30 |

(Continued)

*Primary Examiner* — Matthew M Nelson
(74) *Attorney, Agent, or Firm* — Jinn Su

(57) ABSTRACT

Dental mirrors which are self-cleaning are described. The dental mirror may include an interchangeable tip with a cleaning nozzle configured to direct a fluid such as water and/or air across a surface of a mirror. The dental mirror may also include a valve which can be rotated to adjust a flow of fluid to the cleaning nozzle.

17 Claims, 6 Drawing Sheets

(56) References Cited

U.S. PATENT DOCUMENTS

| | | | | |
|---|---|---|---|---|
| 5,951,284 | A * | 9/1999 | Lake | A61B 1/253 433/31 |
| 6,443,729 | B1 | 9/2002 | Watson | |
| 6,485,303 | B1 * | 11/2002 | Goldman | A61C 3/025 433/88 |
| 7,331,785 | B2 * | 2/2008 | Croop | A61B 1/253 433/31 |
| 2005/0282103 | A1 * | 12/2005 | Kwong | A61B 1/247 433/31 |
| 2006/0057538 | A1 * | 3/2006 | Hoeffleur | A61C 3/00 433/72 |
| 2007/0224571 | A1 * | 9/2007 | Watson | A61B 1/253 433/31 |
| 2010/0261132 | A1 * | 10/2010 | Widen | A61B 1/253 433/31 |
| 2011/0033818 | A1 * | 2/2011 | Miller | A61B 1/122 433/31 |
| 2012/0021373 | A1 * | 1/2012 | Moreno | A61B 1/015 433/31 |

* cited by examiner

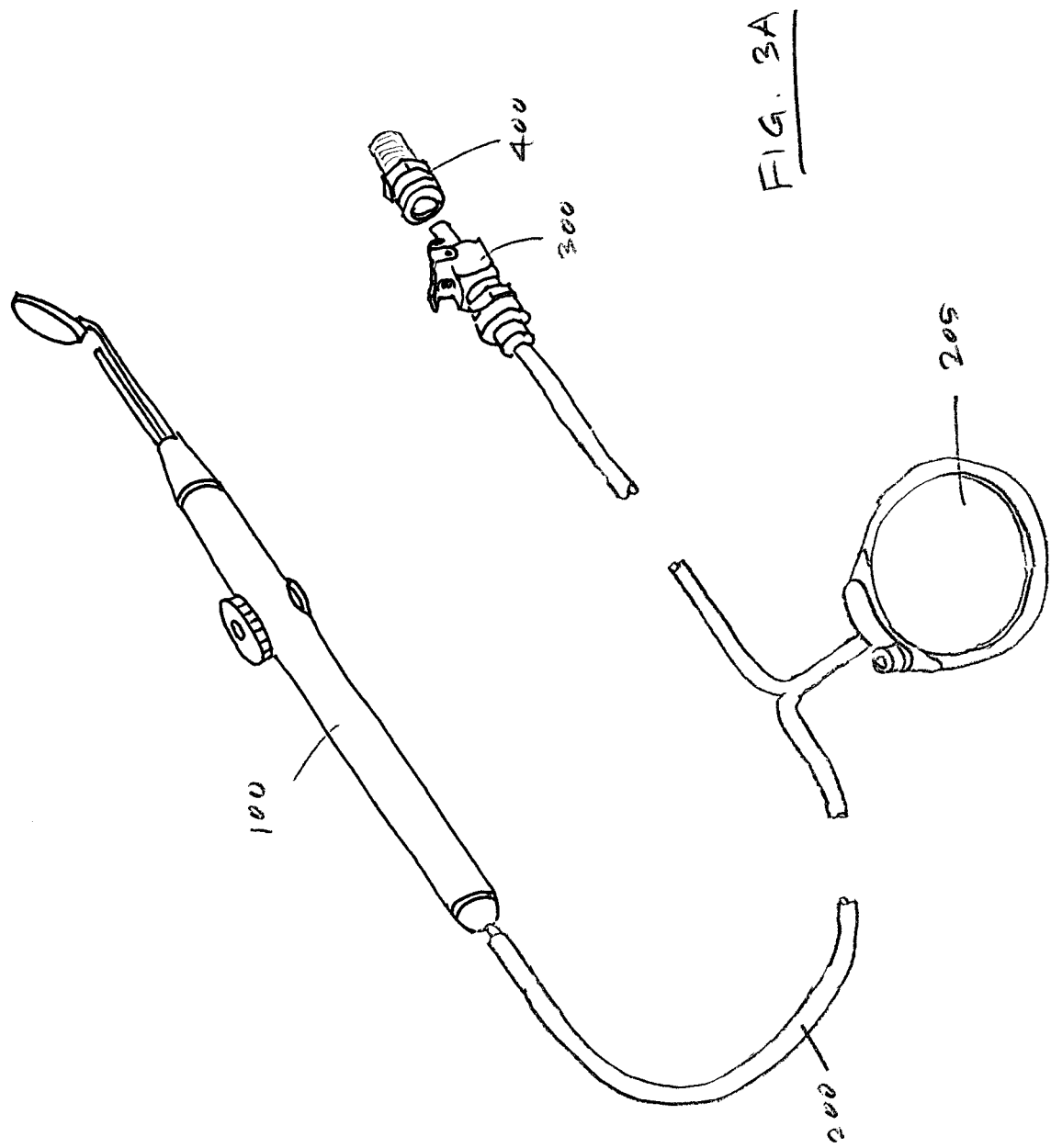

SELF-CLEANING DENTAL MIRRORS

CROSS-REFERENCE TO RELATED APPLICATION

This application claims the benefit of U.S. provisional patent application Ser. No. 61/780,808, filed Mar. 13, 2013, which is hereby incorporated by reference in its entirety.

BACKGROUND

Dental mirrors may be used in the mouth to view areas of interest in the mouth that cannot be seen directly. Dental mirrors may become obscured by saliva, blood, and other bodily fluids. Dental mirrors may also be obscured by dental materials or other byproducts of dental procedures.

Dental mirrors may be cleaned by removing the dental mirror from the mouth, wiping it or otherwise cleaning it, and then re-inserting the dental mirror into the mouth. This manner of cleaning dental mirrors may be time-consuming, especially if repeated cleanings and re-insertions are performed. This manner of cleaning dental mirrors may also cause the user to lose sight and/or focus of an area of interest in the mouth.

What is needed is a dental mirror that allows a user to maintain sight and/or focus of an area of interest in the mouth when the dental mirror is cleaned. What is needed is a dental mirror that does not to be removed from the mouth to be cleaned.

SUMMARY

Dental mirrors of various embodiments are described. In one embodiment, a dental mirror comprises a handle having a proximal portion configured to be coupled to a source of a fluid. The handle has a longitudinal handle lumen. The handle has a substantially transverse valve chamber between a proximal portion and a distal portion of the handle lumen. The dental mirror also comprises a valve rotatably coupled at least partially within the valve chamber. The valve has a body with a channel. The valve has an open configuration wherein the channel is at least partially in fluid communication with the handle lumen and allows the fluid to pass from the proximal portion of the handle lumen to the distal portion of the handle lumen. The valve has a closed configuration wherein the channel is not in fluid communication with the handle lumen and the body prevents the fluid from passing from the proximal portion of the handle lumen to the distal portion of the handle lumen. The dental mirror also comprises an interchangeable tip removably coupled to a distal portion of the handle. The interchangeable tip has a mirror and a cleaning nozzle. The cleaning nozzle has a cleaning lumen in fluid communication with the distal portion of handle lumen. The cleaning nozzle is configured to direct the fluid across a surface of the mirror.

BRIEF DESCRIPTION OF THE DRAWINGS

FIG. 3A shows one embodiment of a dental mirror 100 coupled to a tubing 200 and a quick-disconnect coupling 300.

DESCRIPTION

Figure 1A:
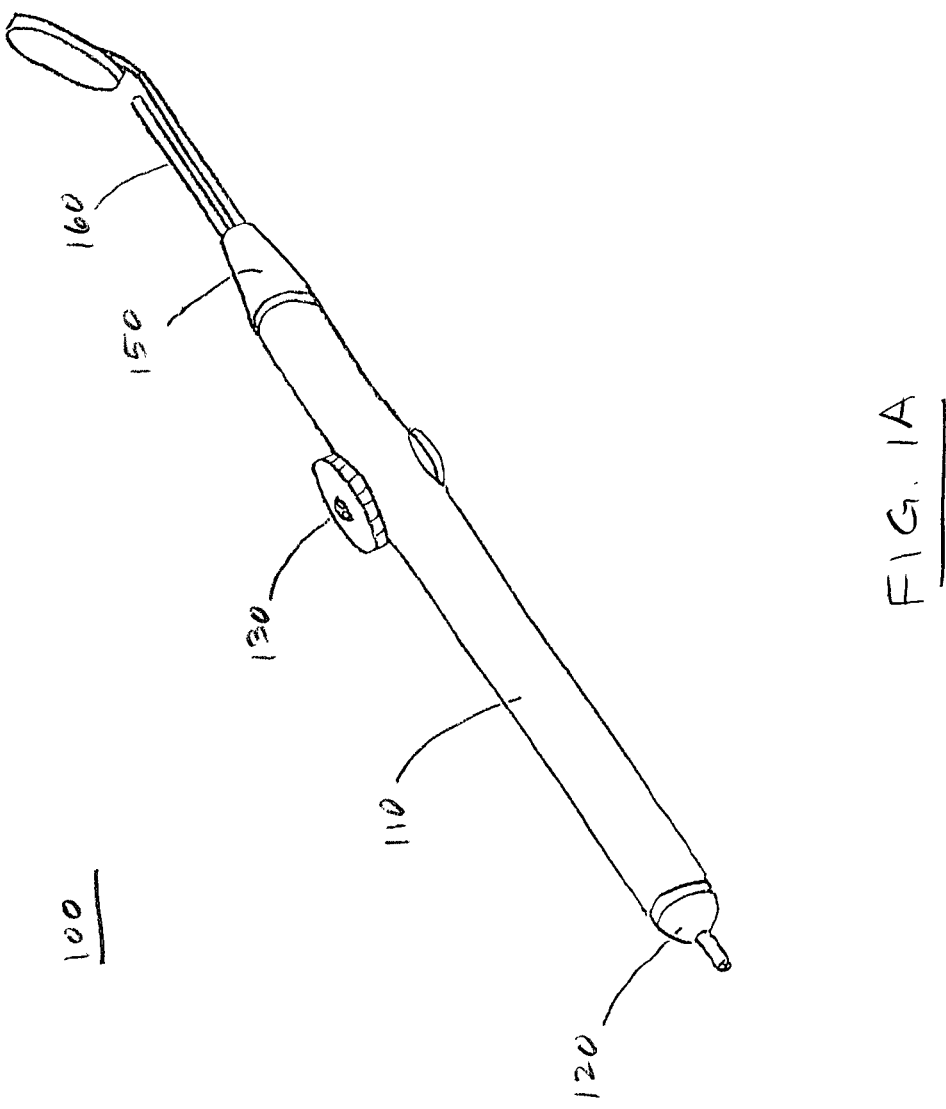
FIGS. 1A-1D show perspective, exploded, top, and side views, respectively, of one embodiment of a dental mirror 100.
Figure 1B:
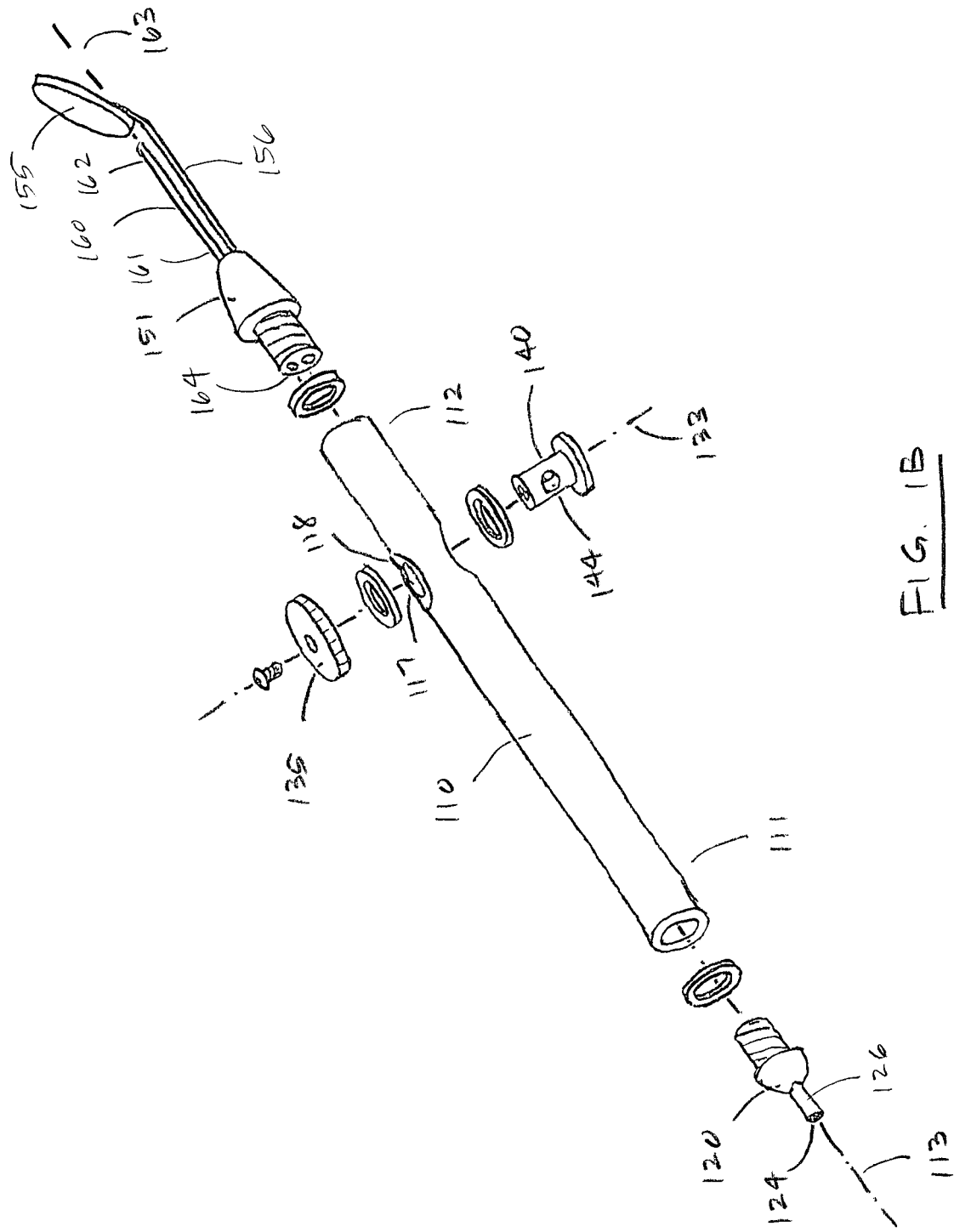
Figure 1C:
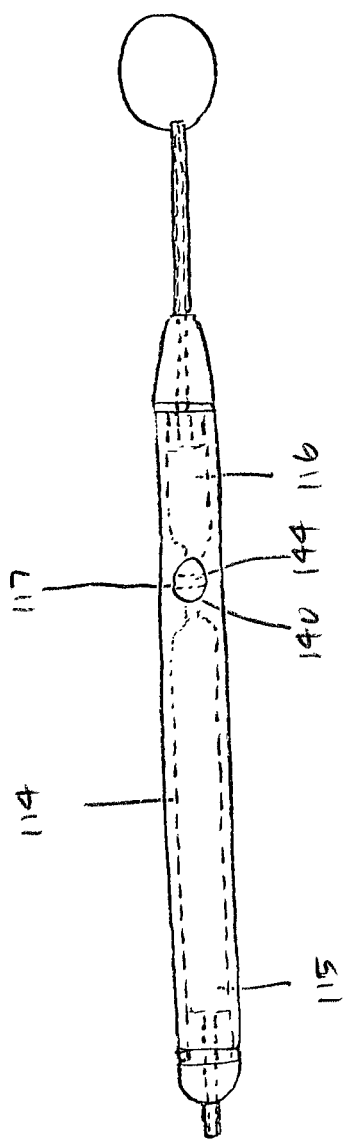
Figure 1D:
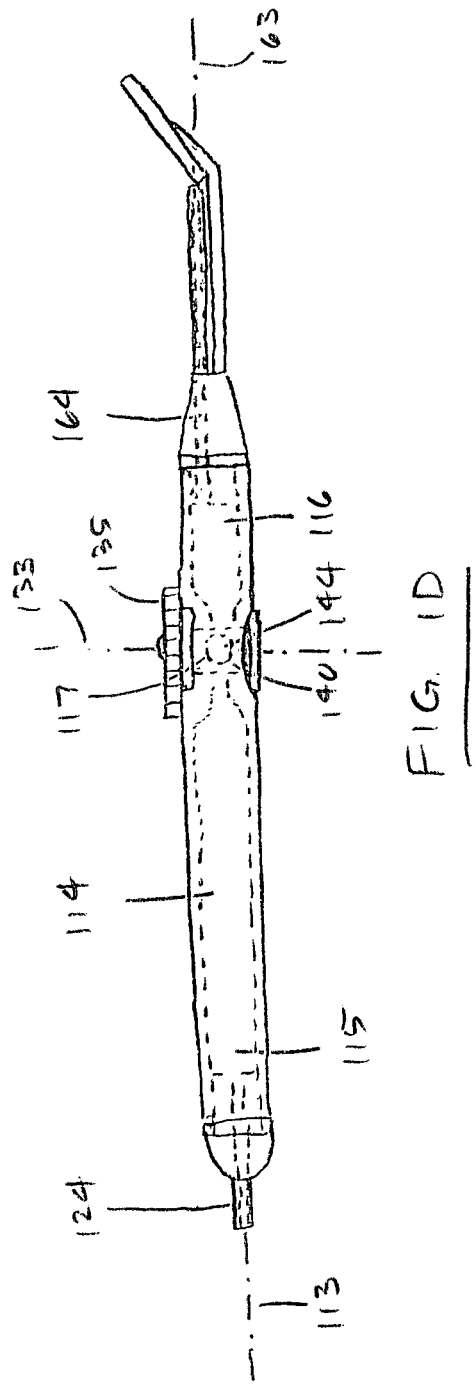

FIG. 1A shows a perspective view of one embodiment of a dental mirror 100. FIG. 1B shows an exploded view of dental mirror 100. FIG. 1C shows a top view of dental mirror 100, with knob 135 removed for clarity. FIG. 1D shows a side view of dental mirror 100.

Dental mirror 100 includes features which allow it to be at least partially cleaned while in use. Dental mirror 100 may include a handle 110, a valve 130, and an interchangeable tip 150 with a cleaning nozzle 160.

Handle 110 may be configured to be held by a user. Handle 110 may include a proximal portion 111, a distal portion 112, a longitudinal axis 113, and a handle lumen 114. Handle lumen 114 may be substantially longitudinal. Handle lumen 114 may include a proximal portion 115 and a distal portion 116.

Handle 110 may also include a valve chamber 117. Valve chamber 117 may be substantially transverse to a handle lumen 114. Valve chamber 117 may be substantially cylindrical. Handle lumen 114 may taper down or become narrower at or near one or both sides of valve chamber 117.

Handle 110 may also include a proximal cap 120. Proximal cap 120 may be coupled to proximal portion 111 of handle 110. Proximal portion 111 of handle 110 and/or proximal cap 120 may be configured to be coupled to a source of a fluid, including a liquid and/or a gas. Fluid may include air, water, and/or any other suitable fluid. Proximal cap 120 may include a lumen 124 and a tubing connector 126. Tubing connector 126 may be configured to be coupled to a tubing.

Valve 130 may be configured to adjust an amount of fluid passing through handle lumen 114 from proximal portion 115 to distal portion of handle lumen 116. Valve 130 may include an axis of rotation 133, a knob 135, and a body 140. Valve 130 may be rotatably coupled at least partially within valve chamber 117.

Body 140 may include at least a portion that is substantially cylindrical. Body 140 may be configured to be rotatable within valve chamber 117. Knob 135 may be configured to allow a user to rotate body 140 within valve chamber 117. Knob 135 may be positioned within a recess 118 in handle 110. Body 140 may include a channel 144. Channel 144 may be substantially transverse to axis of rotation 133 of valve 130. Channel 144 may include at least a portion that is substantially cylindrical. Alternatively, channel 144 may include at least a portion that is substantially semicylindrical, or any other suitable shape.

Valve 130 may include an open configuration wherein channel 144 is at least partially in fluid communication with proximal portion 115 and distal portion 116 of handle lumen 114, and allows fluid to pass from proximal portion 115 to distal portion 116 of handle lumen 114. In a fully open configuration, body 140 may be rotated within valve chamber 117 such that channel 144 is substantially aligned with handle lumen 114.

Valve 130 may also include a closed configuration wherein channel 144 is not in fluid communication with proximal portion 115 and/or distal portion 116 of handle lumen 114, and body 140 prevents fluid from passing from proximal portion 115 to distal portion 116 of handle lumen 114. In the closed configuration, body 140 may be rotated within valve chamber 117 such that channel 144 is substantially transverse to handle lumen 114.

Valve 130 may be rotated to any position between the open configuration and the closed configuration to adjust a flow of fluid from proximal portion 115 of handle lumen 114 to distal portion 116 of handle lumen 114. Valve 130 may be continuously rotatable. Alternatively, valve 130 may include one or more stops which limit a range of motion through which valve 130 may be rotated. Valve 130 may be adjusted with a rotating motion, which may reduce the likelihood of inadvertent activation or adjustment versus a valve which uses a pushing or pressing motion, such as a valve activated by a button.

Interchangeable tip 150 may allow one or more tools to be used with handle 110. Interchangeable tip 150 may also allow a used or dirty tool to be exchanged for a new or clean tool. Interchangeable tip 150 may be removably coupled to distal portion 112 of handle 110. Interchangeable tip 150 may be coupled to distal portion 112 of handle 110 by a threaded coupling, press fit coupling, snap lock, or any other suitable coupling. Interchangeable tip 150 may include a cap 151. Interchangeable tip 150 may include a mirror 155 coupled to cap 151 by an arm 156. Alternatively, interchangeable tip 150 may include one or more other dental and/or surgical tools. Interchangeable tip 150 may allow mirrors 155 of different sizes and/or configurations to be used.

Interchangeable tip 150 may also include a cleaning nozzle 160. Cleaning nozzle 160 may be configured to direct fluid across a surface of mirror 155. Cleaning nozzle 160 may include a proximal portion 161, a distal portion 162, a longitudinal axis 163, and a cleaning lumen 164. Proximal portion 161 of cleaning nozzle 160 may be coupled to cap 151. Distal portion 162 of cleaning nozzle 160 may be positioned at or near an edge of mirror 155. Distal portion 162 of cleaning nozzle 160 may be substantially circular. Alternatively, distal portion 162 of cleaning nozzle 160 may be flattened, tapered, fan-shaped, or any other suitable shape. Cleaning nozzle 160 may be fixed or adjustable. Cleaning lumen 164 may be in fluid communication with distal portion 116 of handle lumen 114. Cleaning lumen 164 may allow fluid to pass through cleaning nozzle and at least partially clean mirror 155. Cleaning lumen 164 may be smaller than handle lumen 114.

Cleaning nozzle 160 may be substantially straight. Alternatively, cleaning nozzle 160 may include one or more portions that are curved. Longitudinal axis 163 of cleaning nozzle 160 may be substantially parallel to longitudinal axis 113 of handle 110. Interchangeable tip 150 may be rotatable with respect to handle 110 and knob 135 to allow a user to adjust the position of knob 135 with respect to mirror 155. Alternatively, longitudinal axis 163 of cleaning nozzle 160 may be substantially collinear with longitudinal axis 113 of handle 110.

Figure 2A:
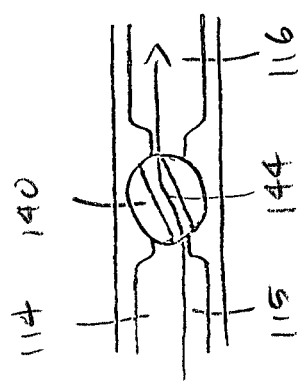
FIGS. 2A-2C show valve 130 in an open, fully open, and closed configurations, respectively.
Figure 2B:
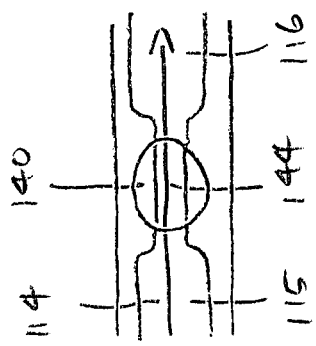
Figure 2C:
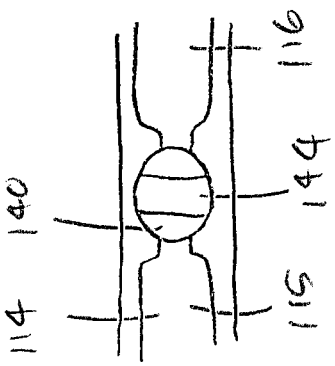

FIGS. 2A-2C show valve 130 in an open, fully open, and closed configurations, respectively.

FIG. 2A shows valve 130 in an open configuration. Body 140 is rotated such that channel 144 is at least partially in fluid communication with proximal portion 115 and distal portion 116 of handle lumen 114, and allows fluid to pass from proximal portion 115 to distal portion 116 of handle lumen 114.

FIG. 2B shows valve 130 in a fully open configuration. Body 140 is rotated such that channel 144 is substantially aligned with handle lumen 114.

FIG. 2C shows valve 130 in a closed configuration. Body 140 is rotated such that channel 144 is not in fluid communication with proximal portion 115 and/or distal portion 116 of handle lumen 114, and body 140 prevents fluid from passing from proximal portion 115 to distal portion 116 of handle lumen 114. Body 140 is rotated such that channel 144 is substantially transverse to handle lumen 114.

Figure 3B:
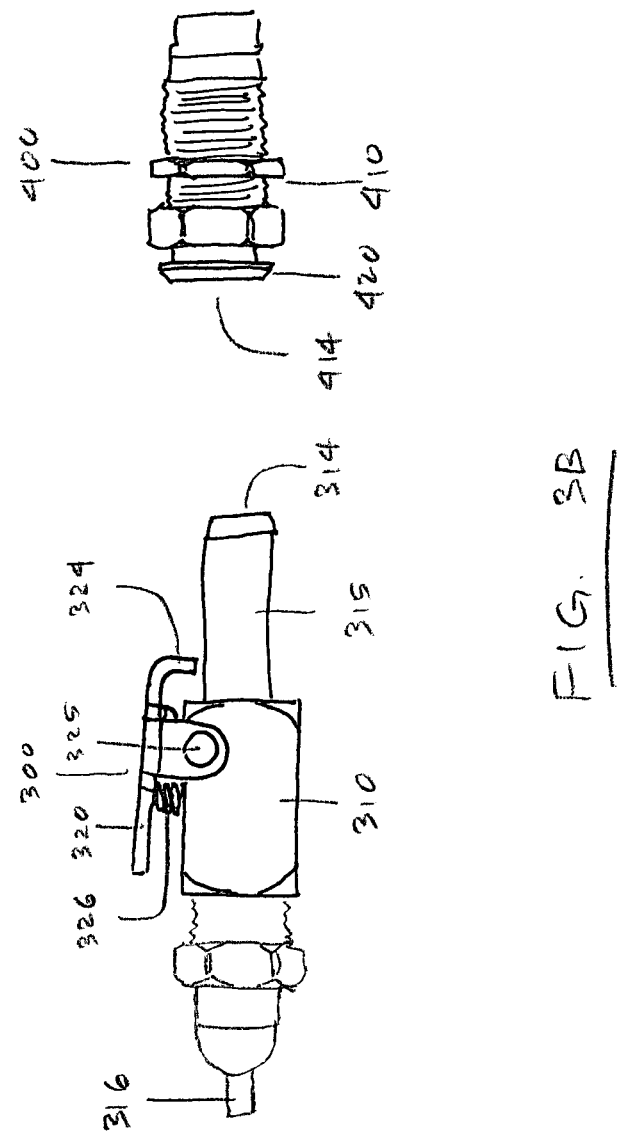
FIG. 3B shows an enlarged view of quick-disconnect coupling 300 and a female coupling 400.

FIG. 3A shows one embodiment of a dental mirror 100 coupled to a tubing 200 and a quick-disconnect coupling 300. FIG. 3B shows an enlarged view of quick-disconnect coupling 300 and a female coupling 400.

Tubing 200 may be flexible or semi-rigid. Tubing 200 may be made of rubber, plastic, or any other suitable material. Tubing 200 may be of any suitable length. A foot pedal 205 may be coupled to tubing. Foot pedal 205 may be coupled in-line with tubing, or in any other suitable manner. Foot pedal 205 may include a valve, and may be configured to adjust an amount of fluid passing through tubing 200. Alternatively, foot pedal 205 may be coupled to the source of fluid and configured to adjust an amount of fluid delivered by the source of fluid. Foot pedal 205 may be used independently of, or in conjunction with, valve 130 to control an amount of fluid delivered to cleaning nozzle 160. For example, valve 130 may be at least partially opened and not adjusted again, and an amount of fluid delivered to cleaning nozzle 160 may be adjusted by using foot pedal 205. As another example, both valve 130 and foot pedal 205 may be used together to adjust an amount of fluid delivered to cleaning nozzle 160.

Quick-disconnect coupling 300 may allow dental mirror 100 to be quickly and securely coupled to and uncoupled from a fluid source. Quick-disconnect coupling 300 may include a body 310 and a latch 320. Body 310 may include a lumen 314, an extension 315, and a tubing connector 316. Lumen 314 may pass through extension 315. Tubing connector 316 may be configured to be coupled to tubing 200. Latch 320 may include a catch 324, a pivot 325, and a spring 326. Latch 320 may have an open position and a closed position. Spring 326 may be configured to bias latch 320 in a closed position.

Female coupling 400 may include a body 410 and a lip 420. Body 410 may include a lumen 414.

Quick-disconnect coupling 300 may be configured to be coupled to female coupling 400. Extension 315 may be configured to be inserted into lumen 414. Latch 320 may be configured to be coupled to lip 420.

While the foregoing has been with reference to particular embodiments of the invention, it will be appreciated by those skilled in the art that changes in these embodiments may be made without departing from the principles and spirit of the invention.

What is claimed is:

1. A dental mirror, comprising:
   a handle having a proximal portion configured to be coupled to a source of a fluid, the handle having a longitudinal handle lumen, the handle having a substantially transverse valve chamber between a proximal portion and a distal portion of the handle lumen;
   a valve rotatably coupled at least partially within the valve chamber, the valve having a body with a channel, the valve having an open configuration wherein the channel is at least partially in fluid communication with the handle lumen and allows the fluid to pass from the proximal portion of the handle lumen to the distal portion of the handle lumen, the valve having a closed configuration wherein the channel is not in fluid communication with the handle lumen and the body prevents the fluid from passing from the proximal portion of the handle lumen to the distal portion of the handle lumen; and an interchangeable tip removably coupled by a threaded coupling to a distal portion of the handle, the interchangeable tip rotatable with respect to the handle when in use, the interchangeable tip having a mirror and a cleaning nozzle, the cleaning nozzle having a cleaning lumen in fluid communication with the distal portion of the handle lumen, the cleaning nozzle configured to direct the fluid across a surface of the mirror.

2. The dental mirror of claim 1, wherein the handle lumen tapers down at or near the valve chamber.

3. The dental mirror of claim 1, wherein the cleaning nozzle has a distal opening positioned at an edge of the mirror.

4. The dental mirror of claim 1, wherein at least a portion of the channel is substantially cylindrical.

5. The dental mirror of claim 1, wherein at least a portion of the channel is substantially semicylindrical.

6. The dental mirror of claim 1, wherein the cleaning nozzle is not coaxial with the handle.

7. The dental mirror of claim 1, wherein the handle defines a single handle lumen.

8. The dental mirror of claim 1, wherein the handle lumen is defined by an outer wall of the handle.

9. A dental mirror, comprising:
a quick-disconnect coupling configured to be coupled to a female coupling and a source of fluid;
a tubing coupled to the quick-disconnect coupling;
a handle having a proximal portion configured to be coupled to the tubing, the handle having a longitudinal handle lumen, the handle having a substantially transverse valve chamber between a proximal portion and a distal portion of the handle lumen;
a valve rotatably coupled at least partially within the valve chamber, the valve having a body with a channel, the valve having an open configuration wherein the channel is at least partially in fluid communication with the handle lumen and allows the fluid to pass from the proximal portion of the handle lumen to the distal portion of the handle lumen, the valve having a closed configuration wherein the channel is not in fluid communication with the handle lumen and the body prevents the fluid from passing from the proximal portion of the handle lumen to the distal portion of the handle lumen; and
an interchangeable tip removably coupled by a threaded coupling to a distal portion of the handle, the interchangeable tip rotatable with respect to the handle when in use, the interchangeable tip having a mirror and a cleaning nozzle, the cleaning nozzle having a cleaning lumen in fluid communication with the distal portion of the handle lumen, the cleaning nozzle configured to direct the fluid across a surface of the mirror.

10. The dental mirror of claim 9, wherein the handle lumen tapers down at or near the valve chamber.

11. The dental mirror of claim 9, wherein the cleaning nozzle has a distal opening positioned at an edge of the mirror.

12. The dental mirror of claim 9, wherein at least a portion of the channel is substantially cylindrical.

13. The dental mirror of claim 9, wherein at least a portion of the channel is substantially semicylindrical.

14. The dental mirror of claim 9, further comprising a foot pedal coupled to the tubing, the foot pedal configured to adjust an amount of fluid passing through the tubing.

15. The dental mirror of claim 9, wherein the cleaning nozzle is not coaxial with the handle.

16. The dental mirror of claim 9, wherein the handle defines a single handle lumen.

17. The dental mirror of claim 9, wherein the handle lumen is defined by an outer wall of the handle.

* * * * *